United States Patent

Meyer

Patent Number: 5,377,005
Date of Patent: Dec. 27, 1994

[54] METHOD FOR MEASURING PARTICLE SIZE OF A DISPERSED PHASE IN A FLUID STREAM

[75] Inventor: James P. Meyer, Plano, Tex.

[73] Assignee: Atlantic Richfield Company, Los Angeles, Calif.

[21] Appl. No.: 115,386

[22] Filed: Sep. 1, 1993

[51] Int. Cl.⁵ ............................................. G01N 15/02
[52] U.S. Cl. .................................. 356/335; 356/441; 250/574; 250/575; 73/61.71; 73/865.5
[58] Field of Search .............................. 356/335—343, 356/440, 70, 436, 441, 442, 73; 250/574, 576, 222.2, 575, 573; 73/61.71, 865.5, 61.41, 61.43, 61.69; 364/555, 571.01

[56] References Cited

U.S. PATENT DOCUMENTS

| | | | |
|---|---|---|---|
| 4,078,863 | 3/1978 | Eriksson et al. | 356/340 |
| 4,420,256 | 12/1983 | Fladda et al. | 356/341 |
| 4,768,879 | 9/1988 | McLachlan et al. | 356/335 |
| 5,036,212 | 7/1991 | Staudinger | 356/441 |
| 5,104,228 | 4/1992 | Baillie | 356/442 |
| 5,245,200 | 9/1993 | Fladda | 356/336 |

*Primary Examiner*—Hoa D. Pham
*Attorney, Agent, or Firm*—Michael E. Martin

[57] ABSTRACT

The mean particle size of a dispersed phase, such as a liquid dispersed in a carrier liquid, is determined by selecting a particulate solids material which, when dispersed in the carrier liquid, has the same refractive index as the dispersed liquid in the carrier liquid, measuring the turbidity of selected particle sizes of the particulate solid for different concentrations of each particle size in the carrier liquid and developing a relationship of the ratio of the turbidity to the concentration for each particle size as a function of particle size which may be referenced when measuring the turbidity and concentration of the dispersed liquid in the carrier liquid to determine the actual particle size of the dispersed liquid.

7 Claims, 2 Drawing Sheets

METHOD FOR MEASURING PARTICLE SIZE OF A DISPERSED PHASE IN A FLUID STREAM

BACKGROUND OF THE INVENTION

1. Field of the Invention

The present invention pertains to a method for measuring the mean particle size of a dispersed phase in a fluid stream such as oil in water, or vice versa, or fine solids dispersed in a liquid, for example.

2. Background

Many fluid treatment processes require or benefit from knowledge of the particle size of a dispersed phase in a carrier liquid. For example, the particle size of oil droplets dispersed in water is important to know to design and operate effective oil-water separation systems. The separation efficiency of many particle removal or separation devices is dependent on the size distribution of the dispersed phase in the continuous or carrier fluid. In this regard, it is desirable to obtain an accurate estimate of the particle size distribution or at least an accurate estimate of the mean particle size of the dispersed phase.

Measurement of particle size of solids particulates dispersed in a fluid may be relatively easily obtained by withdrawing a sample of the fluid from a flowstream and separating the suspended material to measure the particle size. However, for a dispersed liquid, such as oil, in a carrier or continuous phase liquid, such as water, the sample withdrawal and particle separation procedure cannot be carried out since the very act of collecting a sample entails quiescence of the carrier liquid that leads to irreversible coalescence and alteration of the particle size distribution of the dispersed phase. The present invention provides a unique solution to the above-mentioned problem.

SUMMARY OF THE INVENTION

The present invention provides a method for measuring the mean particle size of a dispersed phase in a fluid stream, such as a liquid which is immiscible in another liquid and is uniformly dispersed. The invention is also useful for measuring dispersed particulate solids in a fluid stream.

In accordance with an important aspect of the present invention, a method for measuring a characteristic mean particle size of a dispersed phase in a fluid stream is carried out based on the discovery that the mean particle size of a dispersed phase is dependent on a relationship between the turbidity of the fluid stream and the concentration of the dispersed phase in the fluid stream. In accordance with the present invention, it has also been established that a linear relationship exists between the ratio of the turbidity, in terms of the nephelometric turbidity unit (NTU), to the concentration of the dispersed phase and the dispersed phase particle size for a "mono" dispersed phase or the mean particle size for a "poly" dispersed phase. Accordingly, continuous "on-line" measurement of particle size of a dispersed phase in a flowstream, such as oil dispersed in water, may be carried out by measuring the turbidity of the flowstream, the concentration of the dispersed phase in the carrier fluid and by comparing the ratio of the turbidity measurement to the concentration with the particle size of the particular dispersed phase in question in the carrier fluid in question. In particular, calibration curves may be developed using a range of particle sizes of a particulate material which, in a carrier liquid, presents the same refractive index as the fluid being measured.

The system and method of the present invention permits accurate, "on-line" measurement of the mean particle size of a dispersed liquid phase in a carrier liquid or fluid in an in situ manner without requiring collection or preservation of a fluid sample. The knowledge of the in situ size distribution of a dispersed phase can then be used to provide suitable particle separation equipment or methodology and as a method of continuously monitoring the parameters of a process.

Those skilled in the art will recognize the above-described features and advantages of the invention as well as other superior aspects thereof upon reading the detailed description which follows in conjunction with the drawing.

DESCRIPTION OF PREFERRED EMBODIMENTS

Figure 1:
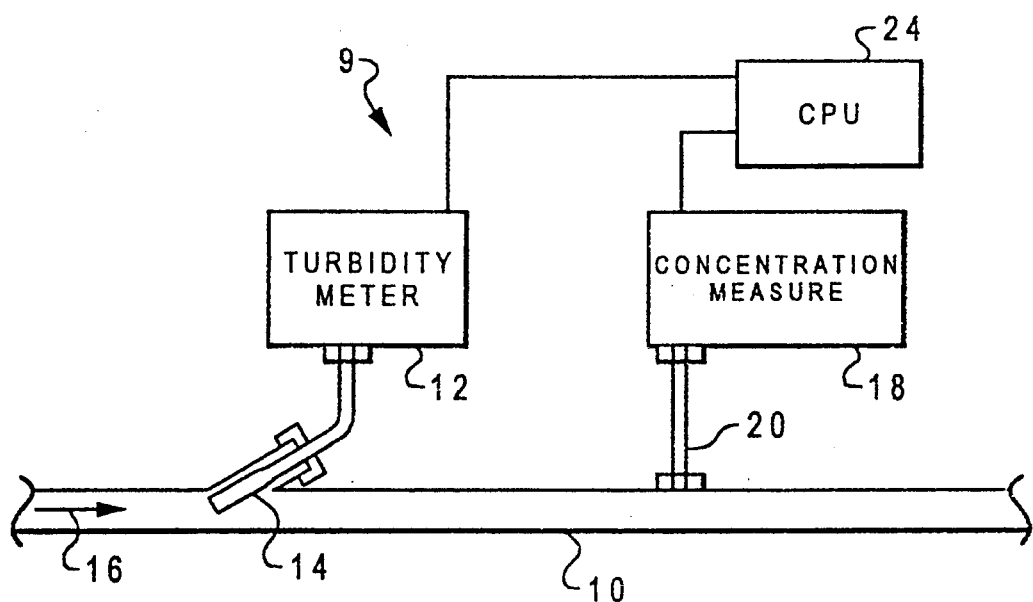
FIG. 1 is a schematic diagram showing the major components of a system for measuring the particle size distribution of a dispersed phase in a fluid flowstream.

FIG. 1 illustrates, in schematic form, a system 9 for measuring the particle size of a mono dispersed phase in a fluid flowstream or the mean particle size of a poly dispersed phase in a fluid flowstream. The system 9 illustrated in FIG. 1 includes a suitable conduit 10 for conducting a fluid flowstream therethrough which includes a dispersed phase such as fine particulate solids or a liquid in the fluid flowstream. For example, it is important to know the particle size of a dispersed phase such as crude or refined oil in water to modify certain processes including separation processes for separating the oil from the water. In this regard, a turbidity meter 12 is provided which includes a suitable probe 14 disposed in the conduit 10 in such a way that it measures the turbidity of fluid flowing through the conduit, such as a water flowstream having a dispersed phase of oil droplets or fine particulate solids therein. The turbidity meter 12 may be of a type commercially available and adapted to continuously measure the turbidity of the flowstream flowing in the direction of the arrow 16 through the conduit 10. One example of a commercial turbidity meter which may be used to practice the method of the present invention may be a series MET or MEX manufactured by BTG, Inc., The Woodlands, Texas. This type of turbidity meter is adapted for in-line measurement of medium to low turbidities of liquid mixtures, such as oil in water. The meter 12 is adapted to measure turbidity up to 1000 NTU's (nephelometric turbidity units).

The system 9 also includes an apparatus 18 for measuring the concentration of the dispersed phase in the fluid flowstream, including oil in water. The apparatus 18 may also be of a type commercially available such as a model OMS-40 Concentration Analyzer commercially available from GSA G. Schmied Abwassertechnik, GmbH, Stuhr, Germany. The above-mentioned apparatus 18 works on the principle of solvent extraction of oil from water with subsequent near infrared spectroscopic analysis of the extracted sample. The apparatus 18 is adapted to operate on a substantially continuous basis by obtaining samples of the fluid flowing through the conduit 10 by way of a sample conduit 20 connected to the apparatus. The apparatus 18 is microprocessor controlled to provide output concentrations in units of milligrams per liter which may be converted to parts per million, for example. Output signals from the turbidity meter 12 and the concentration measuring apparatus 18 may be transmitted to a digital computer or central processing unit 24 whereby certain calculations may be made and compared with a predetermined relationship between the particle size and the calculated parameter in accordance with the present invention.

Figure 2:
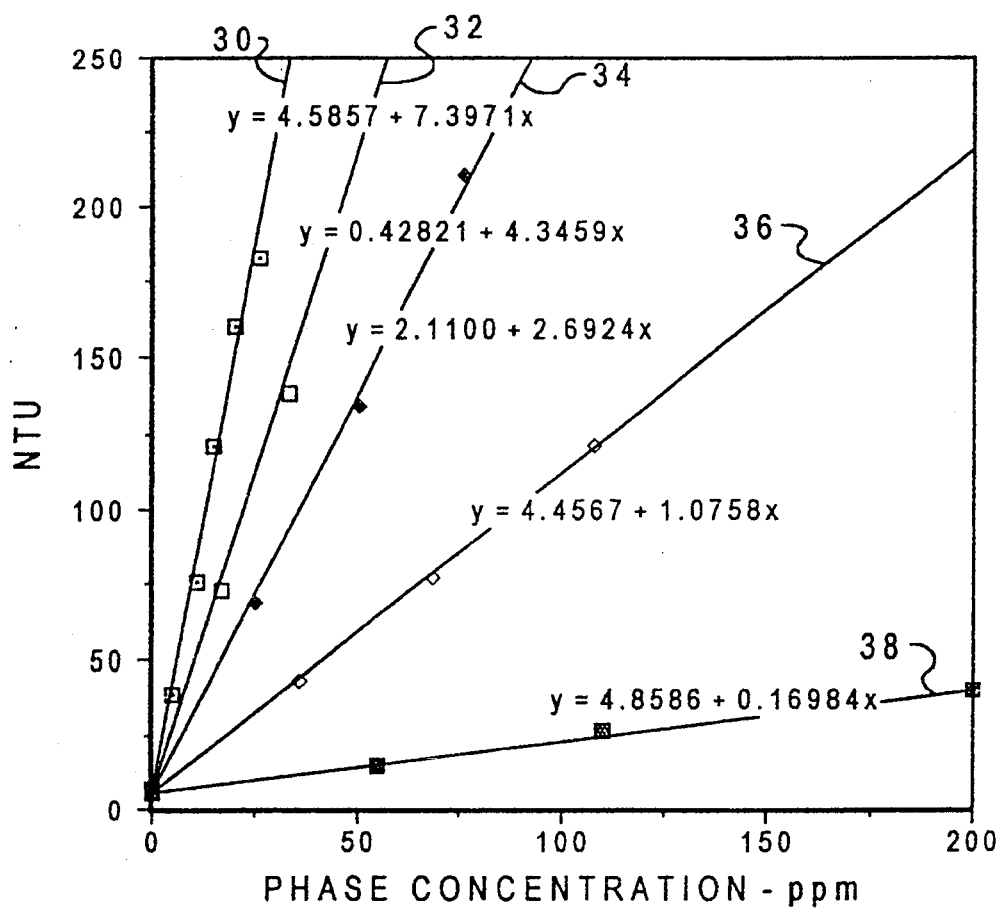
FIG. 2 is a diagram showing the nephelometric turbidity unit (NTU) value versus phase concentration for a particular dispersed phase in a fluid flowstream.

The present invention indicates that a unique relationship exists between the particle size of a mono dispersed phase, or the mean particle size of a poly dispersed phase in a fluid and the amount of light scattered (turbidity) at a particular concentration of the dispersed phase. This relationship is indicated in FIG. 2 wherein the phase concentration of a quantity of fine particulate solids in water is linearly proportional to the turbidity measurement in nephelometric turbidity units (NTU). For example, in conducting tests in accordance with the present invention, selected quantities of polystyrene spheres of different diameters were dispersed in water to develop the curves 30, 32, 34, 36 and 38 of FIG. 2. The particle sizes of the dispersed phase for the curves 30, 32, 34, 36 and 38 were 1 micron, 2 microns, 4 microns, 8 microns and 16 microns, respectively. If a turbidity measurement device such as the meter 12 is used to measure turbidity, it is necessary to use dispersed materials which, in developing the calibration curves of FIG. 2, in the carrier or continuous phase fluid, provide the same refractive index as the dispersed material of interest in its carrier fluid. For example, if it is desired to be able to determine the particle size of a dispersed liquid, such as crude oil in water, a particulate material used to establish the calibration curves of FIG. 2 should, when dispersed in a carrier or continuous phase liquid, such as water, provide the same refractive index as oil in water. The curves of FIG. 2 indicate that, considering the overall scale of the nephelometric turbidity units, the intercept of these curves with the ordinate or "y" axis is virtually zero for zero concentration of the dispersed phase. The actual relationship is indicated for each curve on the diagram of FIG. 2. Accordingly, the ratio of the nephelometric turbidity units to the phase concentration in parts per million (ppm) may be conveniently computed and used to determine particle size, as will be indicated from the discussion hereinbelow.

Figure 3:
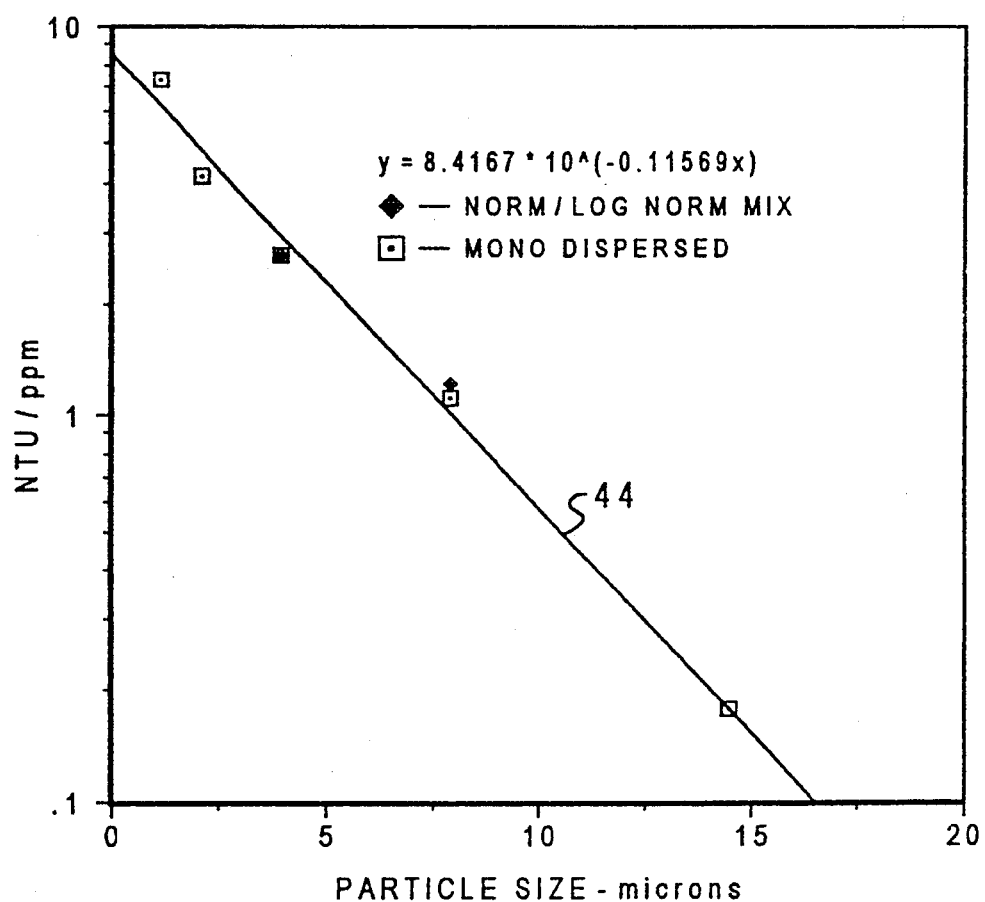
FIG. 3 is a diagram illustrating the relationship between the ratio of turbidity to concentration and the particle size of a particular dispersed phase in a particular fluid.

FIG. 3 illustrates a semilogarithmic plot of the ratio of the NTU (nephelometric turbidity unit) to the phase concentration in ppm (parts per million). As will be noted from FIG. 3, there is a linear relationship, on a semilogarithmic scale, of the ratio of the turbidity measurement unit to the dispersed phase concentration with respect to the particle size of a mono dispersed phase. In order to verify the efficacy of the discovery of the present invention, a test was conducted using a system similar to that of FIG. 1 with selected quantities of polystyrene spheres of four different particle sizes dispersed in water using a normal distribution and a logarithmic-normal distribution. Table I below gives the amounts of mono dispersed materials used to form the poly dispersed mixtures of two different mean particle sizes of 4 um and 8 um, respectively, for the two distributions noted.

TABLE I

| solution mean particle size | Volumes in ml of 200 ppm solution in 100 ml total volume | | | |
|---|---|---|---|---|
| | 2 um | 4 um | 8 um | 16 um |
| 4 um - normal | 7.5 | 41.4 | 1.1 | 0.0 |
| 8 um - normal | 0 | 7.5 | 41.1 | 1.1 |
| 4 um - lognormal | 15 | 20 | 15 | 0 |
| 8 um - lognormal | 0 | 15 | 20 | 15 |

The relationships of FIG. 3 with respect to mean particle size, using the distributions of Table I, fall essentially on the curve 44, indicating a linear relationship of mean particle size of a poly dispersed phase corresponding to the particle size of a mono dispersed phase. Accordingly, the particle size of a mono dispersed phase and the mean particle size of a poly dispersed phase in a fluid flowstream may be determined with a high degree of accuracy in accordance with the method of the present invention.

The system and method of the present invention provides for accurate measurement of the mean particle size of a dispersed liquid phase in a carrier liquid in a manner which does not require collection or preservation of a sample. As such, a real time measurement is capable of being provided while circumventing the inherent problems associated with the coalescence and alteration of particle size distribution which occurs with dispersed phases or emulsions such as oil in water. Moreover, knowledge of the particle size distribution can be used as an indicator to assure that particle separation process and equipment are adequately sized and operated to acquire the desired degree of phase separation.

Although a preferred system and method in accordance with the present invention have been described hereinabove, those skilled in the art will recognize that various substitutions and modifications may be made to the preferred embodiment without departing from the scope and spirit of the invention as recited in the appended claims.

What is claimed is:

1. A method for determining the particle size of a dispersed phase in a fluid comprising the steps of:

measuring the turbidity of the fluid including the dispersed phase therein;

measuring the concentration of the dispersed phase in the fluid;

calculating the ratio of the turbidity of said fluid with respect to the concentration of said dispersed phase;

measuring the turbidity as a function of the concentration of a dispersion of particulate solids dispersed in a carrier liquid such that when said particulate solids are dispersed in said carrier liquid, said carrier liquid presents the same refractive index as said fluid presents with said dispersed phase therein;

comparing the turbidity of the dispersion of particulate solids in said carrier liquid for selected concentrations of said particulate solids at selected particle sizes;

comparing the ratio of the turbidity to the particle concentration to the particle size of said dispersion of particulate solids to establish a curve defining a relationship between said ratio and said particle size; and determining the particle size of the dispersed phase based on the value of said ratio of said turbidity of said fluid to said concentration of said dispersed phase and the corresponding particle size value determined from said curve.

2. The method set forth in claim 1 wherein:
the fluid is a liquid and the dispersed phase is a liquid.

3. The method set forth in claim 1 wherein:
the fluid is a liquid and the dispersed phase is particulate solids.

4. A method of determining the mean particle size of one liquid which is dispersed in another liquid comprising the steps of:

measuring the turbidity as a function of the concentration of a dispersed phase of particulate solids of a predetermined number of selected particle sizes dispersed in a carrier liquid such that when said particulate solids are dispersed in said carrier liquid, said carrier liquid presents the same refractive index as said another liquid presents with said one liquid dispersed therein;

comparing the turbidity of the dispersed phase of particulate solids in said carrier liquid for selected concentrations of said dispersed phase of particulate solids at selected particle sizes;

comparing the ratio of the turbidity to the particle concentration to the particle size of said particulate solids to establish a curve defining a relationship between said ratio and said particle size;

measuring the turbidity of said one liquid in said another liquid;

measuring the concentration of said one liquid in said another liquid; and comparing the ratio of the turbidity of said one liquid in said another liquid to the concentration of said one liquid in said another liquid with said curve defining said relationship to determine the particle size of said one liquid in said another liquid.

5. The method set forth in claim 4 wherein:
said one liquid is oil and said another liquid is water.

6. The method set forth in claim 5 wherein:
said dispersed phase of particulate solids comprises polystyrene spheres of selected particle sizes dispersed in water comprising said carrier liquid.

7. A method for determining the mean particle size of a dispersed phase comprising oil dispersed in water comprising the steps of:

selecting a particulate solids material of predetermined plural particle sizes which, when dispersed in water, will provide a mixture having the same refractive index as a mixture of said oil dispersed in water;

measuring the turbidity of selected concentrations of said particulate solids dispersed in water in selected ones of said particle sizes;

comparing the ratios of turbidity with respect to the concentration of the selected particle sizes of said particulate solids with the particle size of said particulate solids to establish a relationship between said ratio and said particle size;

measuring the turbidity of a mixture of said oil dispersed in water;

measuring the concentration of said oil dispersed in water; and comparing the ratio of said turbidity of said mixture of said oil dispersed in water with said concentration of said oil dispersed in water and comparing said ratio with said relationship to determine the particle size of said oil in said mixture.

* * * * *